US009939506B2

(12) United States Patent
Venkataramanan et al.

(10) Patent No.: US 9,939,506 B2
(45) Date of Patent: Apr. 10, 2018

(54) METHODS OF INVESTIGATING FORMATION SAMPLES USING NMR DATA

(71) Applicant: Schlumberger Technology Corporation, Sugar Land, TX (US)

(72) Inventors: Lalitha Venkataramanan, Lexington, MA (US); Fred K. Gruber, Boston, MA (US); Tarek M. Habashy, Burlington, MA (US); Ridvan Akkurt, Lexington, MA (US); Badarinadh Vissapragada, Walpole, MA (US); Richard E. Lewis, Frisco, TX (US); Erik Rylander, Frisco, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 728 days.

(21) Appl. No.: 14/406,503

(22) PCT Filed: May 24, 2013

(86) PCT No.: PCT/US2013/042621
§ 371 (c)(1),
(2) Date: Dec. 8, 2014

(87) PCT Pub. No.: WO2013/184404
PCT Pub. Date: Dec. 12, 2013

(65) Prior Publication Data
US 2015/0177351 A1  Jun. 25, 2015

Related U.S. Application Data

(60) Provisional application No. 61/657,527, filed on Jun. 8, 2012.

(51) Int. Cl.
*G01R 33/54* (2006.01)
*G01V 3/14* (2006.01)
(Continued)

(52) U.S. Cl.
CPC ............ *G01R 33/54* (2013.01); *G01N 24/08* (2013.01); *G01N 24/081* (2013.01);
(Continued)

(58) Field of Classification Search
USPC ......................... 324/300–322; 600/407–435; 382/128–131
See application file for complete search history.

(56) References Cited

U.S. PATENT DOCUMENTS 5,486,762 A * 1/1996 Freedman ............ G01N 24/081
324/303
9,753,176 B2 * 9/2017 Datey ...................... G01V 3/32
(Continued)

FOREIGN PATENT DOCUMENTS

WO   2013184404 A1   12/2013

OTHER PUBLICATIONS

Venkataramanan, et al. "Solving Fredholm Integrals of the First Kind With Tensor Product Structure in 2 and 2.5 Dimensions," IEEE Transactions on Signal Processing, vol. 50, No. 5, May 2002, pp. 1017-1026.
(Continued)

*Primary Examiner* — Melissa Koval
*Assistant Examiner* — Tiffany Fetzner

(57) ABSTRACT

A methods are provided for investigating a sample containing hydrocarbons by subjecting the sample to a nuclear magnetic resonance (NMR) sequence using NMR equipment, using the NMR equipment to detect signals from the sample in response to the NMR sequence, analyzing the signals to extract a distribution of relaxation times (or diffusions), and computing a value for a parameter of the sample as a function of at least one of the relaxation times (or diffusions), wherein the computing utilizes a correction factor that modifies the value for the parameter as a function
(Continued)

of relaxation time for at least short relaxation times (or as a function of diffusion for at least large diffusion coefficients).

10 Claims, 17 Drawing Sheets

(51) Int. Cl.
  *G01V 3/32*   (2006.01)
  *G01V 3/38*   (2006.01)
  *G01N 24/08*   (2006.01)
  *G01R 33/44*   (2006.01)

(52) U.S. Cl.
  CPC ............ *G01R 33/448* (2013.01); *G01V 3/14* (2013.01); *G01V 3/32* (2013.01); *G01V 3/38* (2013.01)

(56) References Cited

U.S. PATENT DOCUMENTS

| | | |
|---|---|---|
| 2003/0057947 A1 | 3/2003 | Ni et al. |
| 2003/0214286 A1 | 11/2003 | Heidler |
| 2004/0189296 A1 | 9/2004 | Sun et al. |
| 2004/0222791 A1 | 11/2004 | Chen |
| 2005/0040822 A1 | 2/2005 | Heaton |
| 2010/0277165 A1 | 11/2010 | Freedman |
| 2010/0315081 A1 | 12/2010 | Chanpura et al. |
| 2012/0074934 A1 | 3/2012 | Green |
| 2013/0060474 A1 | 3/2013 | Venkataramanan et al. |
| 2013/0179083 A1 | 7/2013 | Gruber et al. |
| 2014/0229112 A1* | 8/2014 | Datey .................... E21B 47/00 702/7 |
| 2015/0177351 A1* | 6/2015 | Venkataramanan ..... G01V 3/14 324/309 |

OTHER PUBLICATIONS

Cheng, et al. "Power-law relationship between the Viscosity of Heavy Oils and NMR relaxation," SPWLA 50th Annual Logging Symposium, Jun. 24-24, 2009, pp. 1-7.

Galatsanos, et al. "Methods for Choosing the Regularization Parameter and Estimating the Noise Variance in Image Restoration and Their Relation," IEEE Transactions on Image Processsing, vol. 1, No. 3, Jul. 1992, pp. 322-336.

Herron et al. "Real-Time Petrophysical Analysis in Siliciclastics from the Integration of Spectroscopy and Triple-Combo Logging," SPE 77631, SPE Annual Technical Conf. and Exhibition, San Antonio, Texas, U.S.A., Sep. 29-Oct. 2, 2002, pp. 1-7.

Songergeld, et al. "Micro-Structural Studies of Gas-Shales," SPE-131771, SPE Unconventional Gas Conference, Pittsburgh, Pennsylvania, U.S.A., Feb. 23-25, 2010, pp. 1-17.

Kausik, et al. "Characterization of Gas Dynamics in Kerogen Nanopores by NMR," SPE-147198, SPE Annual Technical Conference and Exhibition, Denver, Colorado, U.S.A., Oct. 30-Nov. 2, 2011, pp. 1-16.

McKeon, et al. "An improved NMR tool design for fasting logging," SPWLA 40th Annual Logging Symposium, May 30-Jun. 3, 1999, pp. 1-14.

Schmoker, et al. Organic Carbon in Bakken Formation, United States Portion of the Williston Basin, The American Association of Petroleum Geologists Bulletin, vol. 67, No. 12, Dec. 1983, pp. 2165-2174.

Examination Report issued in corresponding Gulf Council application GC2013-24592 dated Jan. 25, 2017. 4 pages.

Grattoni, et al., "An Improved Technique for Driving Drainage Capillary Pressure from NMR T2 Distributions", Sep. 22, 2003, Proceedings of the International Symposium of the Society of Core Analysts, SCA2003, 12 pages.

Ranhong, et al., "The influence factors of NMR logging porosity in complex fluid reservoir", Oct. 1, 2008, Science in China Series D: Earth Sciences, vol. 51, No. S2, pp. 212-217.

Wilson, et al., "Relationship between susceptibility induced field inhomogeneities, restricted diffusion, and relaxation in sedimentary rocks", Aug. 4, 2006, Journal of Magnetic Resonance, Academic Press, Orlando, FL, vol. 183, No. 1, pp. 1-12.

Mitchell, et al., "Obtaining true transverse relaxation time distributions in high-field NMR measurements of saturated porous media: Removing the influence of internal gradients", Jun. 28, 2010, Journal of Chemical Physics, American Institute of Physics, vol. 132, No. 24, 10 pages.

Hook, et al., "SPE 146883 Improved Precision Magnetic Resonance Acquisition: Application to Shale Evaluation", Oct. 30-Nov. 2, 2011, Proceedings of the SPE Annual Technical Conference and Exhibition, Denver, CO, 8 pages.

Bachman, et al., "Porosity Determination from NMR Log Data: The Effects of Acquisition Parameters, Noise, and Inversion", Nov. 11-14, 2007, Proceedings of the SPE Annual Technical Conference and Exhibition, Anaheim, CA, 11 pages.

Office Action issued in related EP application 13800446.0 dated Dec. 18, 2015, 7 pages.

European Search Report issued in related EP application 13800446.0 dated Nov. 23, 2015, 6 pages.

Office Action No. 17242 issued in related MX application MX/a/2014/015069 dated Mar. 7, 2016, 7 pages.

International Search Report for International Application No. PCT/US2013/042621 dated Aug. 23, 2013.

* cited by examiner

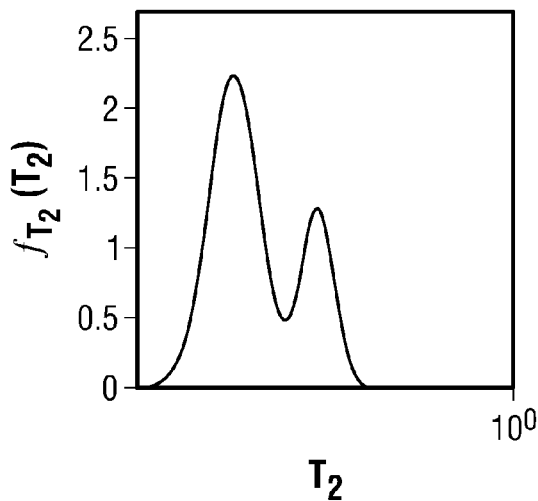
FIG. 2A
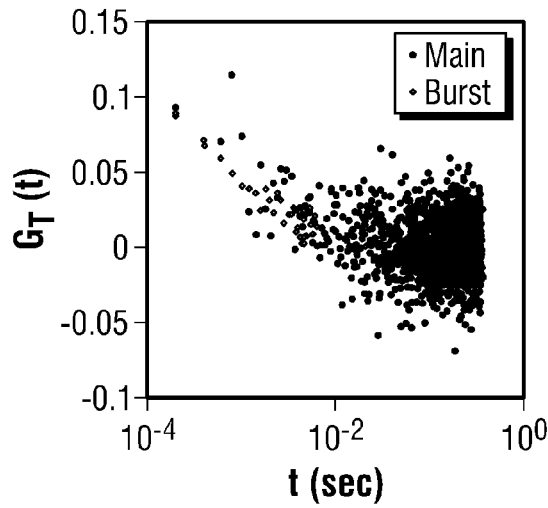
FIG. 2B
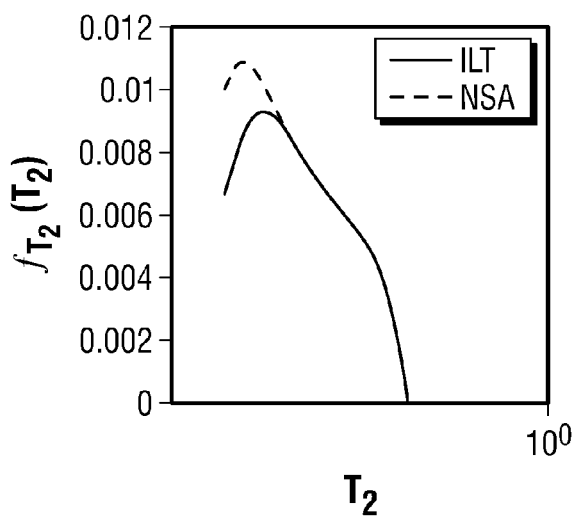
FIG. 2C
Porosity:
$\phi_{true} = 11.0$ pu
$\hat{\phi} = 10.1 \pm 0.7$ pu
$\tilde{\phi}_c = 10.9 \pm 0.8$ pu
T2LM (in ms):
$T_{2, LM, true} = 1.66$
$\hat{T}_{2, LM} = 2.19$
$\tilde{T}_{2, LM, c} = 1.91$
FIG. 2D

METHODS OF INVESTIGATING FORMATION SAMPLES USING NMR DATA

CROSS-REFERENCE TO RELATED APPLICATION

This application is a non-provisional patent application that claims benefit of U.S. Provisional Patent Application Ser. No. 61/657,527 filed Jun. 8, 2012 entitled "Method to Estimate Porosity from NMR Data at Short Relaxation Times." The provisional patent application is incorporated by reference herein.

BACKGROUND

1. Field

This application relates to methods for processing data obtained from nuclear magnetic resonance (NMR) equipment that is used to investigate earth samples containing hydrocarbons. This application more particularly relates to methods for processing NMR tool data obtained from investigating formations containing hydrocarbons that exhibit short relaxation times in order to obtain information regarding one or more characteristics of the formation, although it is not limited thereto.

2. State of the Art

Nuclear magnetic resonance (NMR) tool are used in oilfield applications to enable characterization of petrophysical properties. Low-field relaxation measurements made by the NMR tools are often dominated by short relaxation components, typically on the order of the echo-spacing of the NMR pulse sequence. For example, bulk relaxation of heavy oils often falls below 100 msec. Recent studies indicate that Barnett gas shales contain organic matter in the form of kerogen in various stages of maturation, see C. H. Songergold, et al., "Microstructural Studies of Gas-Shales", *SPWLA 50$^{th}$ Annual Logging Symposium*, 2009, and that there is significant porosity in small pore sizes of the organic matter varying between 5-1000 nm. This results in significant $T_2$ relaxation below 10 msec. Laboratory studies on Haynesville gas-shale cores also provide experimental evidence that fluid is restricted in nanopores resulting in $T_2$ relaxations that are smaller than a few milliseconds. R. Kaushik et al., "Characterization of Gas Dynamics in Kerogen Nanopores by NMR", *SPE*-147198, 2011.

Traditionally, pulse sequences and data inversion are optimized for magnetization data that fall in the middle of the $T_2$ relaxation spectrum; i.e., between 50 ms and 500 ms. To enhance the precision at short relaxation times, data has been acquired according to an "enhanced precision mode" (EPM—a Trademark of Schlumberger). See, D. McKeon et al. "An improved NMR tool design for fasting logging", SPWLA, 1999. This mode involves acquiring magnetization data at at least two different wait times often referred to as "main" and "burst". In addition, improved precision in porosity determinations has been obtained by increasing the number of repeats, and thus improving the signal-to-noise ratio (SNR). See, P. Hook et al., "Improved Precision Magnetic Resonance Acquisition: Application to Shale Evaluation", *SPE*—146883, 2011.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to one aspect, methods are provided for investigating a sample containing hydrocarbons by subjecting the sample to a nuclear magnetic resonance (NMR) sequence using NMR equipment, using the NMR equipment to detect signals from the sample in response to the NMR sequence, analyzing a decay of the signals to extract a distribution of relaxation times, and computing a value for a parameter of the sample as a function of at least one of the relaxation times, wherein the computing utilizes a correction factor that modifies the value for the parameter as a function of relaxation time for at least some short relaxation times, on the same order of magnitude as the echo-spacing of the tool. For purposes herein, the "same order of magnitude" includes a range from one-half the echo spacing to ten times the echo spacing.

In one embodiment, an estimate of porosity of a formation containing hydrocarbons is made by placing an NMR tool in a borehole traversing the formations, conducting downhole experiments to obtain signals over time, analyzing the decay of the signals to extract a $T_2$ distribution, and computing a porosity estimate as a function of $T_2$, where the computing utilizes a correction factor that is a function of relaxation time for at least short relaxation times.

In one embodiment, the correction factor that is used in computing the parameter as a function of relaxation time for at least short relaxation times is a function of normalized bias of the measurement. In one embodiment, the normalized bias of the tool is obtained from the porosity sensitivity curve. For computation of porosity sensitivity curve, see H, N. Bachman et al, "Porosity determination from NMR log data: the effects of acquisition parameters, noise and inversion", SPE—110803, 2007. In another embodiment, the normalized bias is obtained by testing the tool with respect to samples of known parameter values.

In one aspect, improved porosity estimates obtained through the use of a correction factor obtained from the porosity sensitivity curve can be utilized to obtain improved determinations of additional parameters such as, by way of example only, rock permeability, hydrocarbon viscosity, bound and free fluid volumes, etc.

In another aspect, improved porosity estimates obtained through the use of a correction factor that is a function of relaxation time can be used to obtain improved analysis of organic content of a formation.

BRIEF DESCRIPTION OF THE DRAWINGS

FIG. 2A is a graph showing a true $T_2$ distribution.

FIG. 2B shows data simulated through an enhanced precision mode based on the $T_2$ distribution of FIG. 2A.

FIG. 2C is a graph showing an estimated $T_2$ distribution using the data of FIG. 2A generated using an inverse Laplace Transform technique (ILT) and the methods of this application (NSA).

FIG. 2D is a chart showing true porosity and $T_{2LM}$ values and values obtained via ILT and NSA.

DETAILED DESCRIPTION

Figure 1:
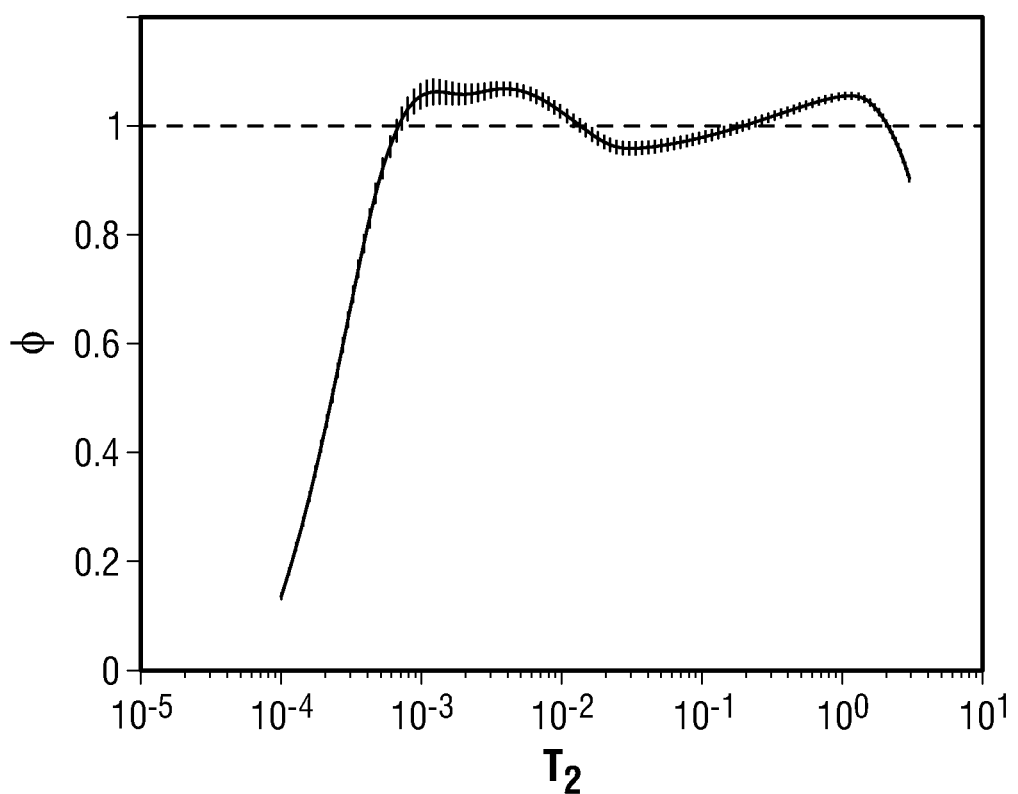
FIG. 1 is porosity sensitivity plot as a function of $T_2$.

A porosity sensitivity curve is seen in FIG. 1. The porosity sensitivity curve is a plot of the estimated porosity obtained from applying with an NMR tool a given pulse sequence, and utilizing a set of acquisition and inversion parameters on the received signal. A porosity sensitivity curve is obtained as follows. For each location of the Dirac-delta function in the $T_2$ domain, the magnetization data with porosity $\phi_T$ are simulated with white Gaussian noise with zero-mean and a standard deviation $\sigma_\varepsilon$. The SNR for the data set is $\phi_T/\sigma_\varepsilon$. The sensitivity curve can be computed a priori and is a function of the pulse sequence (e.g., fully polarized CPMG (Carr-Purcell-Meiboom-Gill), EPM (enhanced precision mode), etc.), data acquisition parameters (e.g., wait times, number of bursts, number of repeats, cable speed, SNR in the data) and inversion parameters (e.g., regularization, lower and upper limits of the discretized relaxation times, the level of discretization, the $T_1/T_2$ ratio).

The measured NMR data are then processed according to an algorithm, such as the Inverse Laplace Transform (ILT) to estimate the T2 distribution $\phi(T_2)$. A description of the ILT algorithm, is provided in H. N. Bachman et al, "Porosity determination from NMR log data: the effect of acquisition parameters, noise, and inversion" SPE—110803, 2007 which is hereby incorporated by reference herein in its entirety. The ILT algorithm or method involves minimizing a cost function Q with respect to the underlying $T_2$ distribution $\phi$ according to $$Q=\|G-L\phi\|^2+\alpha\|(\phi)\|^2 \qquad (1)$$

where G is a vector representing the measured EPM data, L is the matrix relating the $T_2$ distribution to the NMR measurement, and $\phi$ is the discretized version of the underlying density function $\phi(T_2)$. The first term in the cost function is the least squares error between the data and the fit. The second term is referred to as the regularization and incorporates smoothness in the expected relaxation amplitudes.

The parameter a denotes the compromise between the fit to the data and an a priori expectation of the distribution. In equation (1), $\alpha$ is the weight given to the regularization and can be chosen by a number of different methods. See N. P. Galatsanos et al, "Methods for choosing the regularization parameter and estimating the noise variance in image restoration and their relation", IEEE Transactions in Image Processing, vol. 1, No. 3, July 1992. The total corrected porosity is the sum of the porosity over all T2 bins.

The porosity sensitivity curve of FIG. 1 was generated based on an EPM pulse sequence generated from a Dirac delta function with unity porosity, an echo spacing of 200 µs, a main Carr-Purcell-Meiboom-Gill (CPMG) sequence with 1000 echoes and a wait time of 10 s, and a burst with 50 repetitions, 30 echoes, and a wait time of 20 ms. These echoes were contaminated with many noise realizations of white Gaussain noise with standard deviation 0.2. For each of these realizations, the porosity was estimated using regularized nonnegative least squares with Tikhonov regularization. In this plot, an inverse Laplace transform (ILT) with Tikhonov regularization $\alpha=10$ was used. The $T_2$ bins used to analyze the data in FIG. 1 are logarithmically spaced between $T_{2,min}=300$ µs and $T_{2,max}=3$ s.

As seen in FIG. 1, at short relaxation times (e.g., under 1 ms, and more particularly under 0.5 ms) there is a decreased sensitivity (accuracy) which is due to finite echo spacing typically on the order of 200 µs and, therefore, a decreased measured signal amplitude. The decreased sensitivity is also due to the noise in the measurement. At large relaxation times, the sensitivity is small due to finite polarization. At intermediate relaxation times, certain undulations in sensitivity are observed. These undulations are a function of how the inversion handles the data and depend on the $T_1/T_2$ ratios, regularization, and signal to noise ratio (SNR) in the data. Decreased sensitivity at short and long relaxation times, poor SNR in the field-data as well as non-linear aspects of the inversion pose challenges in accurate estimation of parameters from the measured data.

According to one embodiment, the decreased sensitivity at short relaxation times is addressed through the use of a correction factor $c_f(T_2)$ that is a function of $T_2$. In particular, if the estimated porosity from an inversion algorithm is $\hat{\phi}$, then the normalized bias (inaccuracy) B in porosity at a particular relaxation time can be expressed as $$B = \frac{\langle \hat{\phi} \rangle - \phi_T}{\phi_T} \qquad (2)$$

where $\phi_T$ is the true porosity and where <•> is an average computed over many different realizations of noise. In one embodiment, the normalized bias B can be computed from the mean of the porosity obtained from multiple realizations of the data as the location of the Dirac-delta function systematically scans the $T_2$ spectrum. Similarly, the standard deviation $\sigma_\phi$ (or error bar) of the estimated porosity as shown in FIG. 1 can be computed a priori for each location of the Dirac-delta function. Together, the bias and the standard deviation can be used to compute a correction factor $c_f$ to the estimated $T_2$ distribution and porosity as follows. In another embodiment, the normalized bias B is obtained by testing the tool with respect to one or more samples of known parameter values (i.e., one or more calibration samples.

Consider a measured magnetization decay, obtained and analyzed using the same acquisition and inversion parameters used to derive the porosity sensitivity curve. Let $\hat{\phi}(T_2)$ obtained from the non-linear analysis denote the 'binned porosity", referring to the estimated $T_2$ distribution for a specified relaxation time $T_2$. The normalized error can be related to the previously computed normalized bias according to $$B(T_2) \approx \frac{\hat{\phi}(T_2) - \phi_T}{\phi_T}. \tag{3}$$

Thus, the corrected porosity $\phi_c$ is expressed by $$\phi_c(T_2) \approx \phi_T = \frac{\hat{\phi}(T_2)}{1 + B(T_2)}. \tag{4}$$

From relationship (4), it can be seen that a correction factor $c_f(T_2)$ can be computed as $$c_f(T_2) = 1/(1 + B(T_2)). \tag{5}$$

Therefore, a more accurate estimate of porosity at any relaxation time $T_2$ is $$\hat{\phi}_c(T_2) = c_f(T_2)\hat{\phi}(T_2). \tag{6}$$

The corrected porosity is the sum over all the corrected porosity in all $T_2$ bins.

In one embodiment, the role of the correction factor of equation (6) is to amplify the binned porosity where it tends to be under-estimated. In one embodiment, the role of the correction factor of equation (6) is to amplify the binned porosity where it tends to be under-estimated and to reduce the porosity where it is over-estimated. This results in a more uniform sensitivity and accurate estimation of the binned and total porosity over the range of the $T_2$ spectrum.

An alternate expression for the correction factor can be obtained by taking into account the SNR of the $T_2$ distribution at a given $T_2$ according to $$c_f(T_2) = \frac{1}{1 + B(T_2)\frac{R(T_2)}{\beta(R(T_2)) + R(T_2)}} \tag{7}$$

$$\text{where } R(T_2) = \frac{\hat{\phi}(T_2)}{\sigma_\phi(T_2)}. \tag{8}$$

Here $R(T_2)$ corresponds to the SNR for a given $T_2$, $\beta$ is a scalar whose magnitude is typically on the order of unity, and $<>$ is an average computed over $T_2$. When the SNR at any relaxation time is large (signifying high confidence in the presence of that $T_2$ component in the data), the alternate correction factor of equation (7) can be significant and modifies the binned porosity. However, when the SNR at any relaxation time is small (signifying low confidence at that relaxation time), the correction factor tends to a value of 1 and does not appreciably modify the binned porosity.

The use of the SNR in the correction factor (i.e., the alternate correction factor of equation (7)) has particular impact in embodiment having $T_2$ distributions that do not have short relaxation times since the alternate correction factor avoids amplifying artifacts at short relaxation times obtained in the estimated $T_2$ distribution as a result of the non-linear aspects of the inversion algorithm.

The impact of a correction factor, according to equation (7) is seen with reference to FIGS. 2A-2D. In particular, FIG. 2A shows a $T_2$ distribution from which magnetization data are simulated in EPM mode. The true porosity of the $T_2$ distribution (as indicated in FIG. 2D) is 11.0 pu and the simulated main and burst data with additive noise with SNR=5 is shown in FIG. 2B based on an echo spacing of 0.2 ms, a main CPMG with 1800 echoes and a wait time of 2.4 s, and a burst with 10 repetitions, 30 echoes, and a wait time of 20 ms. The results of the analysis on a data set using an inverse Laplace transform (ILT) with standard inversion parameters and $\alpha=10$ assuming 30 bins for the $T_2$ distribution logarithmically spaced between $T_{2,min}=300$ μs and $T_{2,max}=3$ s is seen in FIG. 2C. Also seen in FIG. 2C are the results of an analysis using the same inversion parameters but correcting the ILT with the correction factor (shown and referred to hereinafter as NSA). It is seen that the components corresponding to short relaxation times are enhanced to a small degree with the $T_2$ distribution at intermediate relaxation times has undergone at most neglible change. FIG. 2D shows the true porosity and the true $T_2$ logarithmic mean $T_{2,LM,true}$ as well as the porosity and $T_{2,LM}$ calculated by the ILT analysis ($\hat{\phi}$ and $\hat{T}_{2,LM}$) and the NSA analysis ($\hat{\phi}_c$ and $\hat{T}_{2,LM,c}$). The error bars on the porosity are obtained by Monte-Carlo analysis on data with different noise realizations. As will be appreciated, the porosity calculated by the NSA analysis using the correction factor is much closer to the true porosity $\phi_{true}$ than the porosity calculated by the ILT analysis, and the $T_2$ logarithmic mean is also significantly closer to the true value.

If the normalized root mean square error (NRMSE or e) of the porosity is defined according to $$e = \frac{\sqrt{\langle(\hat{\phi} - \phi_T)^2\rangle}}{\phi_T} \cdot 100 \tag{9}$$

and 100 different noise realizations of the data were obtained from the $T_2$ distribution in FIG. 2A and analyzed using ILT and NSA, using the calculated values set out in FIG. 2D, the NRMSE for the ILT-derived porosity is 10.4% whereas the NRMSE for the corrected NSA-derived porosity was a lower 7.6%.

Figure 3:
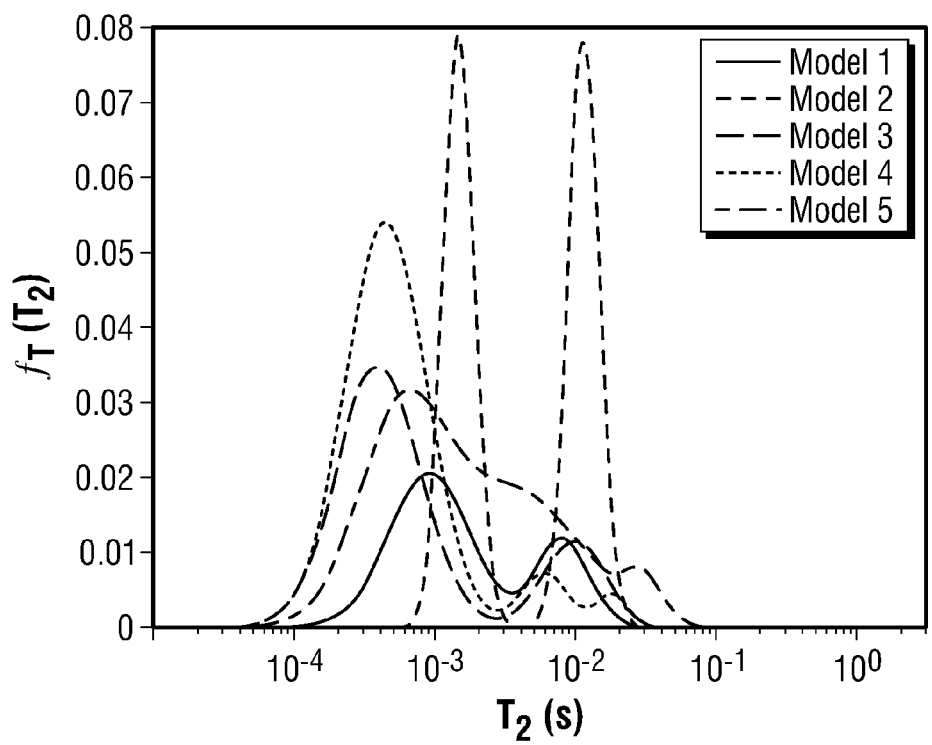
FIG. 3 is a plot of five models of $T_2$ distribution with short relaxation times from which magnetization data are simulated.

Turning to FIG. 3, a plot of five models of $T_2$ distributions with short relaxation times from which magnetization data are simulated is provided. The data are simulated in EPM mode with a SNR=5. The data are calculated with an echo spacing of 0.2 ms, a main CPMG with 1800 echoes and a wait time of 2.4 s, and a burst with 30 echoes and a wait time of 20 ms. The burst is repeated 10 and 50 times (i.e., $N_r=10$ or 50) to provide different sets of data. Data are analyzed using ILT or NSA, assuming 30 bins for the $T_2$ distribution logarithmically spaced between $T_{2,min}$300 μs and $T_{2,max}=3$ s and an automated regularization parameter. See L. Venkataramanan et al., "Solving Fredholm Integrals of the First Kind with Tensor Product Structure in 2 and 2.5 Dimensions, *IEEE Transactions on Signal Processing*, 50:1017-1026 (2002). The results are seen in Table 1 which compares the NMRSE calculated for the ILT and NSA results (100 different data sets with different realizations of noise) for each of the five models. A difference in NRMSE of more than 3% is significant.

TABLE 1

| Model | Processing | NRMSE with $N_r = 10$ | NRMSE with $N_r = 50$ |
|---|---|---|---|
| 1 | NSA | 7.8 | 5.2 |
|   | ILT | 9.8 | 7.7 |
| 2 | NSA | 8.4 | 5.4 |
|   | ILT | 7.3 | 5.5 |
| 3 | NSA | 20 | 17.3 |
|   | ILT | 28 | 24.7 |
| 4 | NSA | 18 | 14 |
|   | ILT | 29 | 23 |
| 5 | NSA | 9 | 7.3 |
|   | ILT | 12 | 10.4 |

As seen in Table 1, the analysis of data using NSA is significantly better than the ILT analysis in several circumstances for all of the models except model 2, and is never significantly worse.

Figure 4:
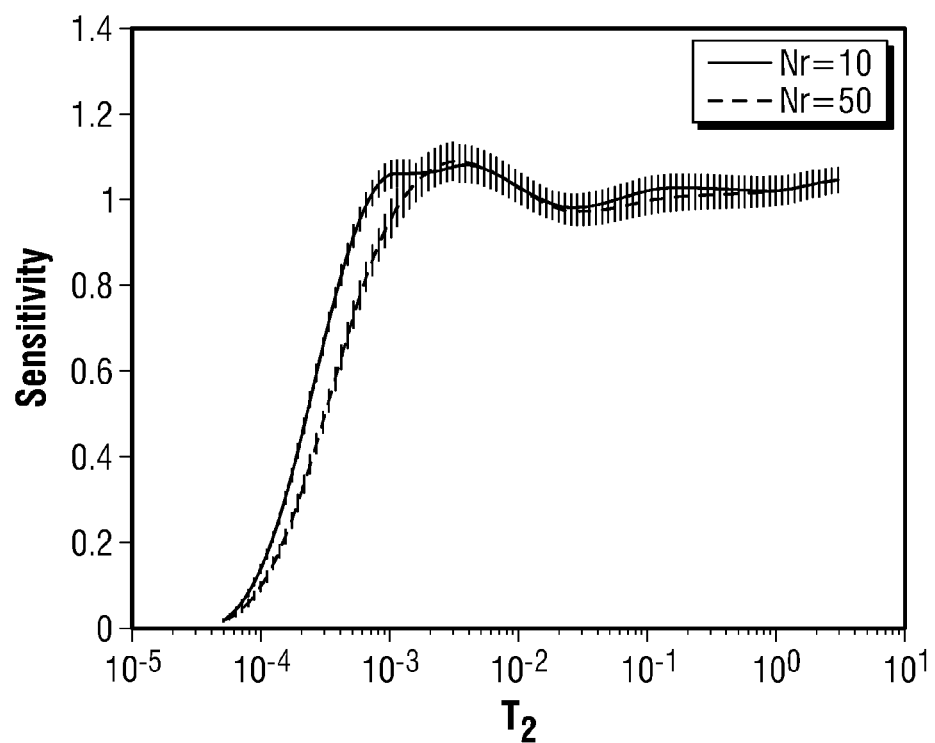
FIG. 4 shows sensitivity curves for 10 and 50 repetitions of a burst.

Columns 3 and 4 of Table 1 show the NRMSE of porosity obtained on data sets with 10 and 50 repeats in the burst, respectively. From Columns 3 and 4 it is seen that a larger number of repeats in the burst leads to an increased SNR and thus a smaller NRMSE, albeit with an increased acquisition time. This is also illustrated in FIG. 4 where the accuracy and precision analyzed with ILT on data with 50 burst repetitions is seen to be better than data acquired with 10 repetitions.

Figure 5:
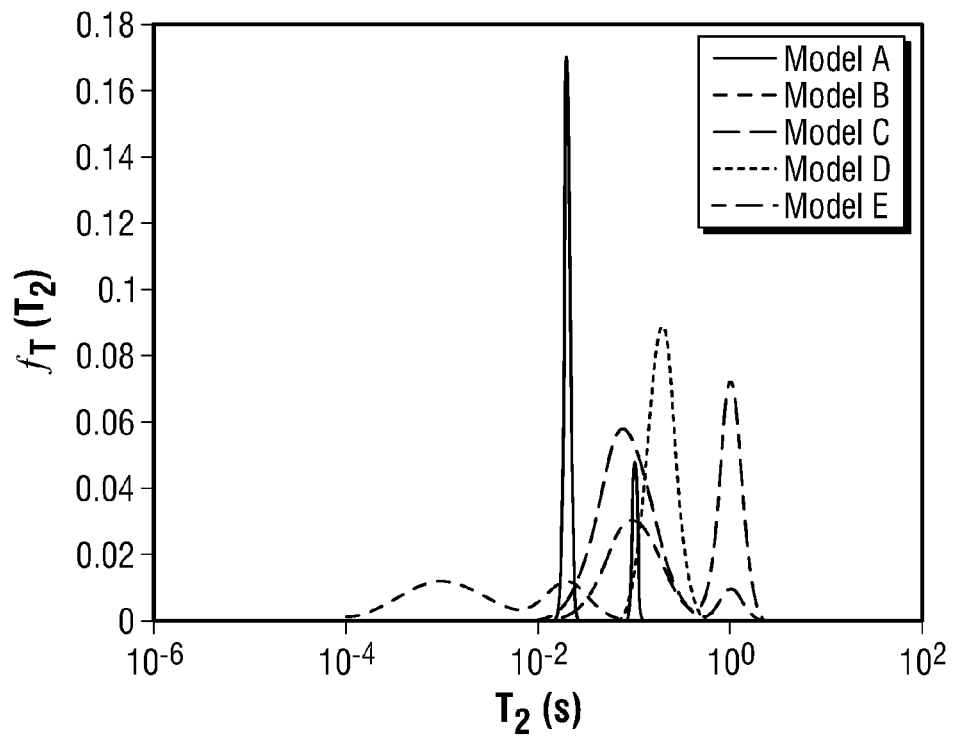
FIG. 5 is a plot of five models of $T_2$ distributions with intermediate and long relaxation times from which magnetization data are simulated.

FIG. 5 is a plot of five models of $T_2$ distributions with intermediate and long relaxation times from which magnetization data are simulated with SNR=5. The EPM pulse sequence is used with 1800 and 30 echoes in the main and burst. The wait times are 2.4 seconds and 20 ms respectively. The echo spacing for the main and burst is 0.2 ms. Data sets with bursts having 10 and 50 repeats were generated.

The data were analyzed using ILT and NSA processing. The default analysis parameters were used with 30 bins in the $T_2$ domain, $T_{2,min}=0.3$ ms, $T_{2,max}=3$ s and automated regularization. The first echo is used in the analysis. The NRMSE obtained from analysis of 100 different data sets simulated from each of the five models is summarized in Table 2. It is seen that for the models having $T_2$ distributions with intermediate and long relaxation times, the results of ILT and NSA processing are comparable as there is no statistically significant difference between the two.

TABLE 2

| Model | Processing | NRMSE with $N_r = 10$ | NRMSE with $N_r = 50$ |
|---|---|---|---|
| A | NSA | 6.9 | 5.1 |
|   | ILT | 6.6 | 5.0 |
| B | NSA | 8.4 | 6.5 |
|   | ILT | 9.3 | 8.4 |
| C | NSA | 6 | 3.8 |
|   | ILT | 5.6 | 3.7 |
| D | NSA | 6.4 | 4 |
|   | ILT | 5.9 | 3.9 |
| E | NSA | 5.3 | 6.7 |
|   | ILT | 5.2 | 6.8 |

Figure 6:
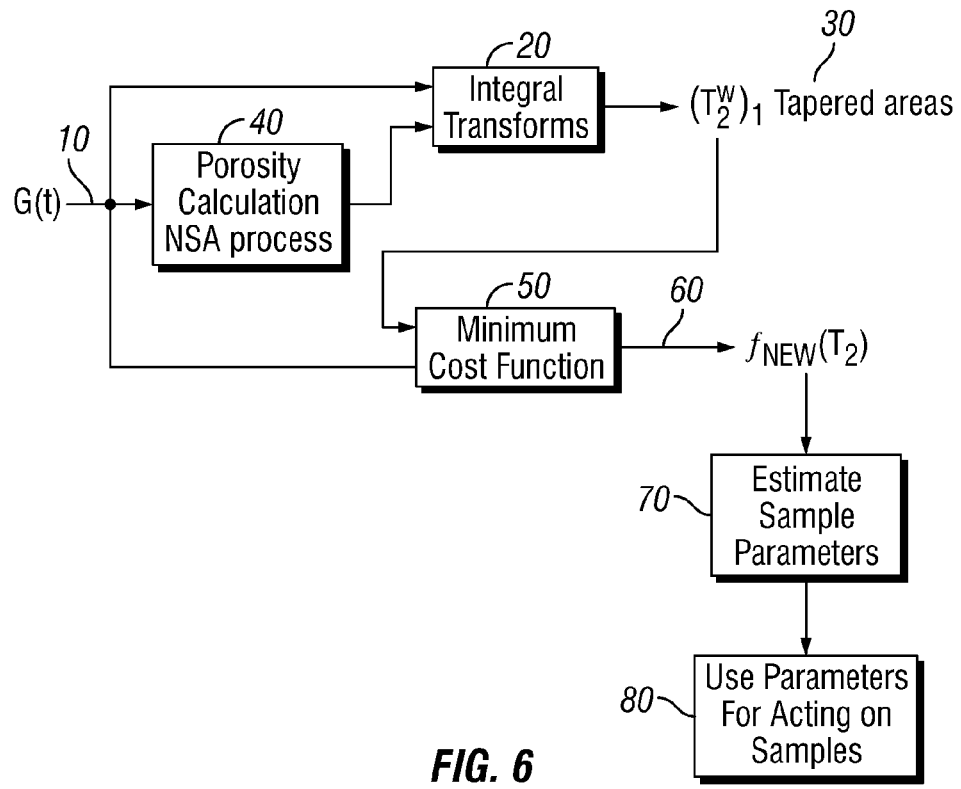
FIG. 6 is a workflow for using an improved determination of porosity to obtain improved determinations of further parameters.

According to one embodiment, the results of NSA processing may be used as part of a method of determining a distribution of a variable that is used to find values of at least one parameter of a sample. More particularly, as seen in FIG. 6 and as disclosed in copending U.S. Ser. No. 13/346,468 filed Jan. 9, 2012 (which is hereby incorporated by reference in its entirety), data G(t) 10 indicative of what might have been measured by an NMR tool as a result of having applied a pulse sequence to a sample is processed using the integral transform approach described in U.S. Ser. No. 13/333,232 (filed Dec. 21, 2011, which is hereby incorporated by reference herein in its entirety) to provide a plurality of linear functionals, e.g., ($T_2^\omega$)), Tapered areas 30. Porosity calculations 40 obtained by processing the NMR data G(t) using NSA processing as described above, are used as an input to the integral transform approach processing 20. The linear functionals obtained at 30 are then used as constraints or "priors" in a cost function 50 incorporating them as Laplace transform elements and utilizing indications of the NMR data in order to generate a $T_2$ distribution denoted $f_{NEW-c}(T_2)$ 60. The calculated $T_2$ distribution is an answer product that may be used for any of many purposes. By way of example only, the $T_2$ distribution 60 may be used at 70 to generate an estimate of one or more parameters or properties of the sample. Where the sample is a rock or a formation, the parameters may include parameters such as rock permeability and/or hydrocarbon viscosity, bound and free fluid volumes, among others. The parameters may then be used at 80, if desired, in models, equations, or otherwise to act on the sample, such as in recovering hydrocarbons from the formation.

Figure 7:
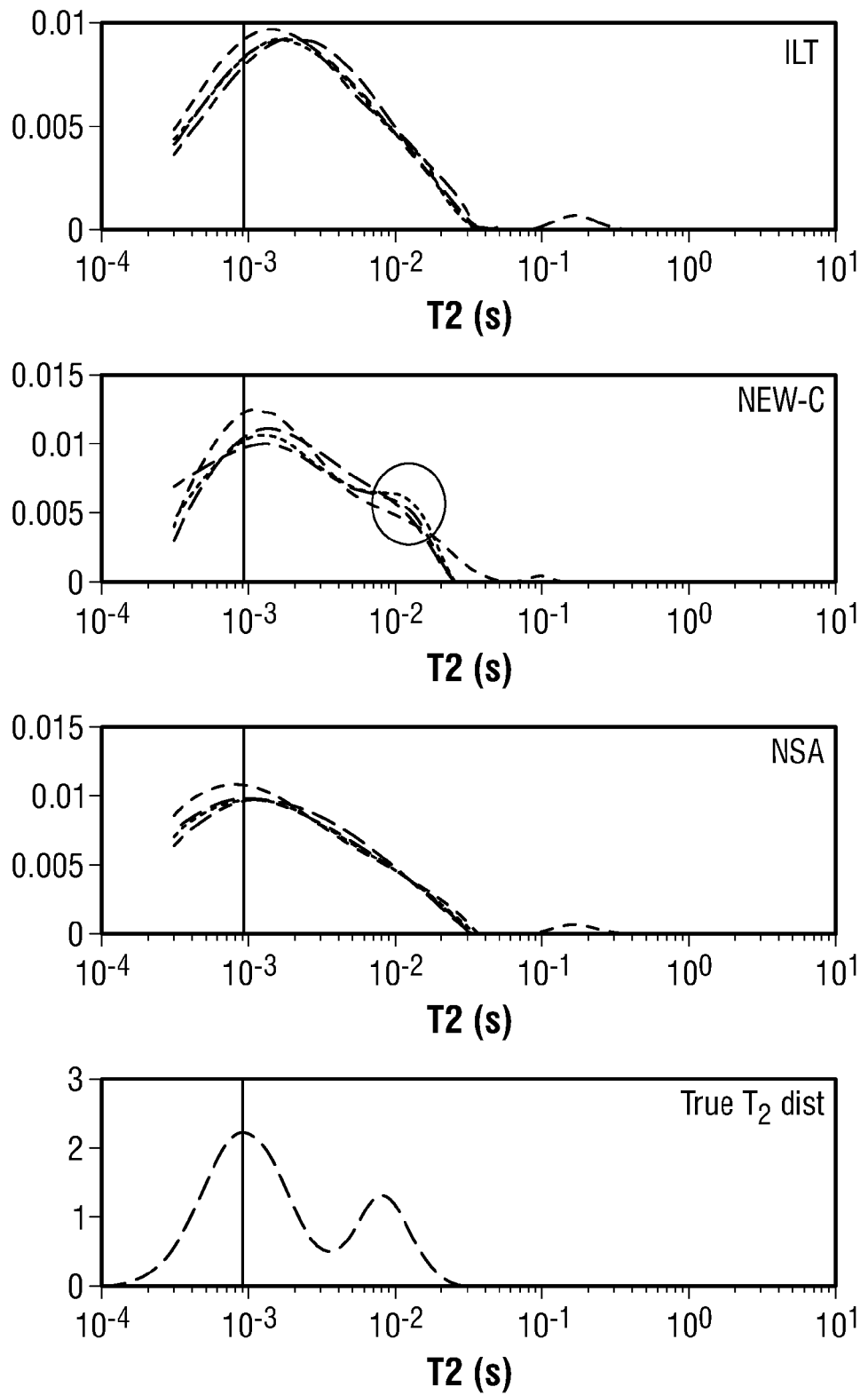
FIG. 7 is a series of graphs showing a true $T_2$ distribution and distributions calculated using different processing techniques with and without the improved determination of porosity as inputs thereto.

FIG. 7 compares the true $T_2$ distribution against the estimated distributions determined using ILT processing, NSA processing, and the processing disclosed in previously incorporated copending U.S. Ser. No. 13/346,468 but utilizing the modified or corrected porosity calculations obtained via NSA processing (NEW-c). As suggested in FIG. 8, the calculated $T_2$ distribution labeled NEW-c has considerably less bias than the $T_2$ distribution obtained using ILT processing (i.e., the peak at short $T_2$'s was closer to the true $T_2$ distribution). In some cases, better resolution was obtained at higher $T_2$'s than as determined by ILT processing and by NSA processing, as indicated by the circled area.

According to another embodiment, instead of minimizing a cost function with respect to $T_2$ to obtain a $T_2$ distribution estimate, a cost function is minimized with respect to a longitudinal relaxation time ($T_1$) to obtain a $T_1$ distribution estimation $f(T_1)$. More specifically, data G(t) is processed using an integral transform approach described in previously incorporated U.S. Ser. No. 13/333,232 to provide a plurality of linear functionals, e.g., ($T_1^\omega$), Tapered areas. Porosity calculations obtained by processing the NMR data G(t) according to NSA processing is used as inputs to the integral transform approach processing. The linear functionals obtained are then used as constraints or "priors" in a cost function incorporating them as well as Laplace transform elements and utilizing indications of the NMR data in order to generate a $T_1$ distribution $f_{NEW-c}(T_1)$. The calculated $T_1$ distribution can be used for any of many purposes such as to generate an estimate of one or more parameters of the sample.

In a similar manner, according to another embodiment, instead of minimizing the cost function with respect to a relaxation time to obtain a relaxation time distribution estimation, a cost function is minimized with respect to NMR diffusion (D) to obtain a D distribution estimation $f(D)$. More specifically, data G(t) is processed using an integral transform approach described in previously incorporated U.S. Ser. No. 13/333,232 to provide a plurality of linear functionals, e.g., ($D^\omega$), Tapered areas. Porosity calculations obtained by processing the NMR data G(t) according to NSA processing is used as inputs to the integral transform approach processing. The linear functionals obtained are then used as constraints or "priors" in a cost function incorporating them as well as Laplace transform elements and utilizing indications of the NMR data in order to generate a D distribution $f_{NEW-c}(D)$. The calculated D distribution can be used for any of many purposes such as to generate an estimate of one or more parameters of the sample.

It will be appreciated that multidimensional distributions may also be extracted using as inputs to the integral transform approach the porosity calculations obtained by processing the NMR data G(t) according to NSA processing.

According to one aspect, NSA processing to obtain improved porosity determinations in samples with short relaxation times may be used to improve an analysis of the organic content of a sample. For example, NSA processing may be used in helping to discriminate organic versus inorganic zones in a formation. More particularly, organic shales, or intervals with total organic carbon exceeding a few percent, are often found intermingled with reservoir and/or non-reservoir intervals which contain no organic matter. Organic zones are identified using NSA total porosity and a matrix adjusted density porosity log available using an Elemental Capture Spectroscopy (ECS) sonde (ECS being a trademark of Schlumberger). See, M. Herron et al., "Real-Time Petrophysical Analysis in Siliciclastics from the Integration of Spectroscopy and Triple-Combo Logging", SPE Annual Technical Conf. and Exhibition, 29 Sep.-2 Oct. 2002. Although kerogen responds as part of the pore space to density porosity tools, magnetic resonance porosity is insensitive to its presence. Thus, the intervals where the NSA total porosity (as measured by a magnetic resonance tool such as the CMR tool of Schlumberger adapted to conduct NSA processing) is less than matrix adjusted density porosity, an organic shale interval can be assumed to be present.

As another example, NSA processing may be used in conjunction with estimating total organic carbon (TOC) in organic shale reservoirs utilizing the "porosity deficit method". More particularly, a density log response to matrix volumes can be written as $$\rho_l = \rho_m(1-V_f-V_k)+\rho_{fa}V_f+\rho_k V_k \quad (10)$$

where $\rho_l$ is the density from the density log in g/cc, $\rho_m$ is the dry matrix density obtained from an ECS channel in g/cc, $\rho_{fa}$ is the apparent fluid density (g/cc) in total pore volume, $\rho_k$ is the kerogen density (g/cc), $V_f$ is the volume hydrocarbon plus total water (V/V), and $V_k$ is the volume kerogen plus unseen bitumen (V/V). The NSA magnetic resonance porosity can be written as $$TCMR_{nsa} = V_f HI_f \quad (11)$$

where TCMR is the total porosity from the Combinable Magnetic Resonance (CMR) tool (CMR is a trademark of Schlumberger) adapted to conduct NSA processing, and $HI_f$ is the hydrogen index of the pore fluid. Combining equations (10) and (11) results in $$V_k = \frac{\rho_m - \rho_l}{\rho_m - \rho_k} - \frac{TCMR_{nsa}(\rho_m - \rho_f)}{HI_f(\rho_m - \rho_k)} \quad (12)$$

where $\rho_f$ is the fluid density.

The kerogen (plus unseen bitumen) volume of equation (11) may be converted to a total organic carbon (TOC) estimation so that comparisons with other estimations of TOC in weight percentage can be made using $$TOC = \frac{V_k}{K_{vr}} \cdot \frac{\rho_k}{\rho_l} \quad (12)$$

where $K_{vr}$ is a maturity constant.

Figure 8:
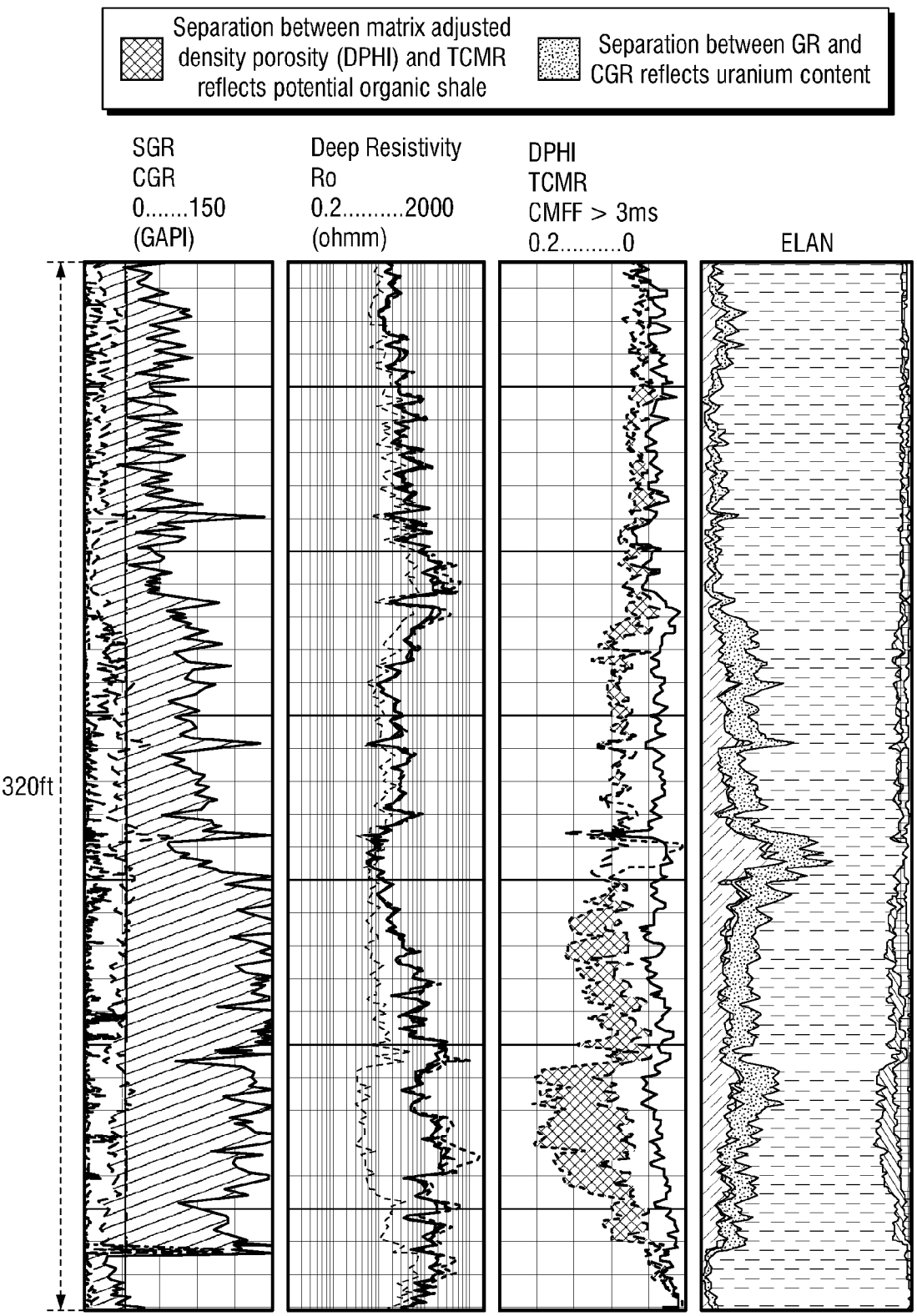
FIG. 8 is a composite view of a shale section which shows separation between density porosity (DPHI) and NMR porosity (TCMR) where the kerogen is present.
Figure 9:
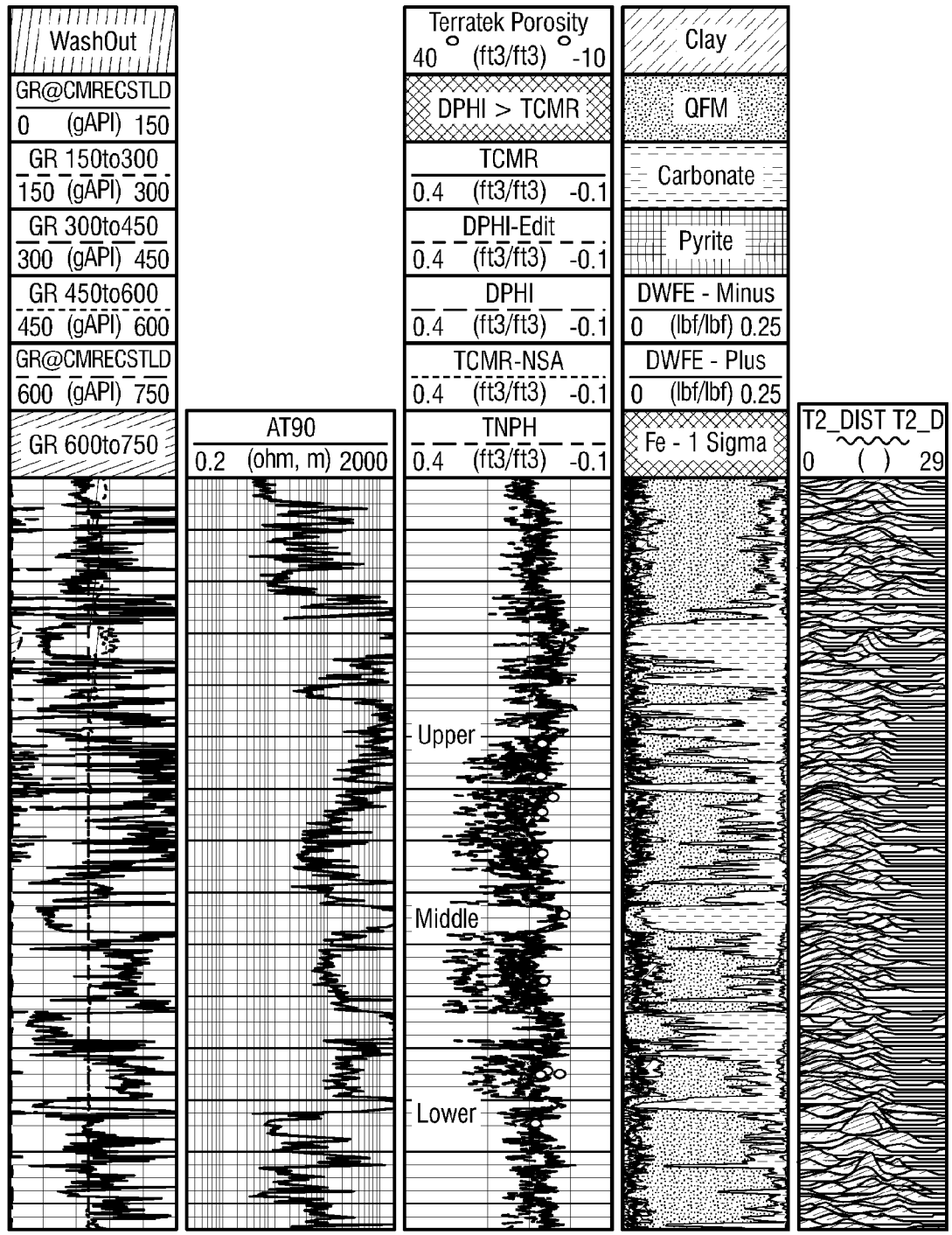
FIG. 9 is a composite view of another well with an appreciable shale section (in the upper, middle and lower levels) which shows separation between DPHI and TCMR where the kerogen is present.
Figure 10A:
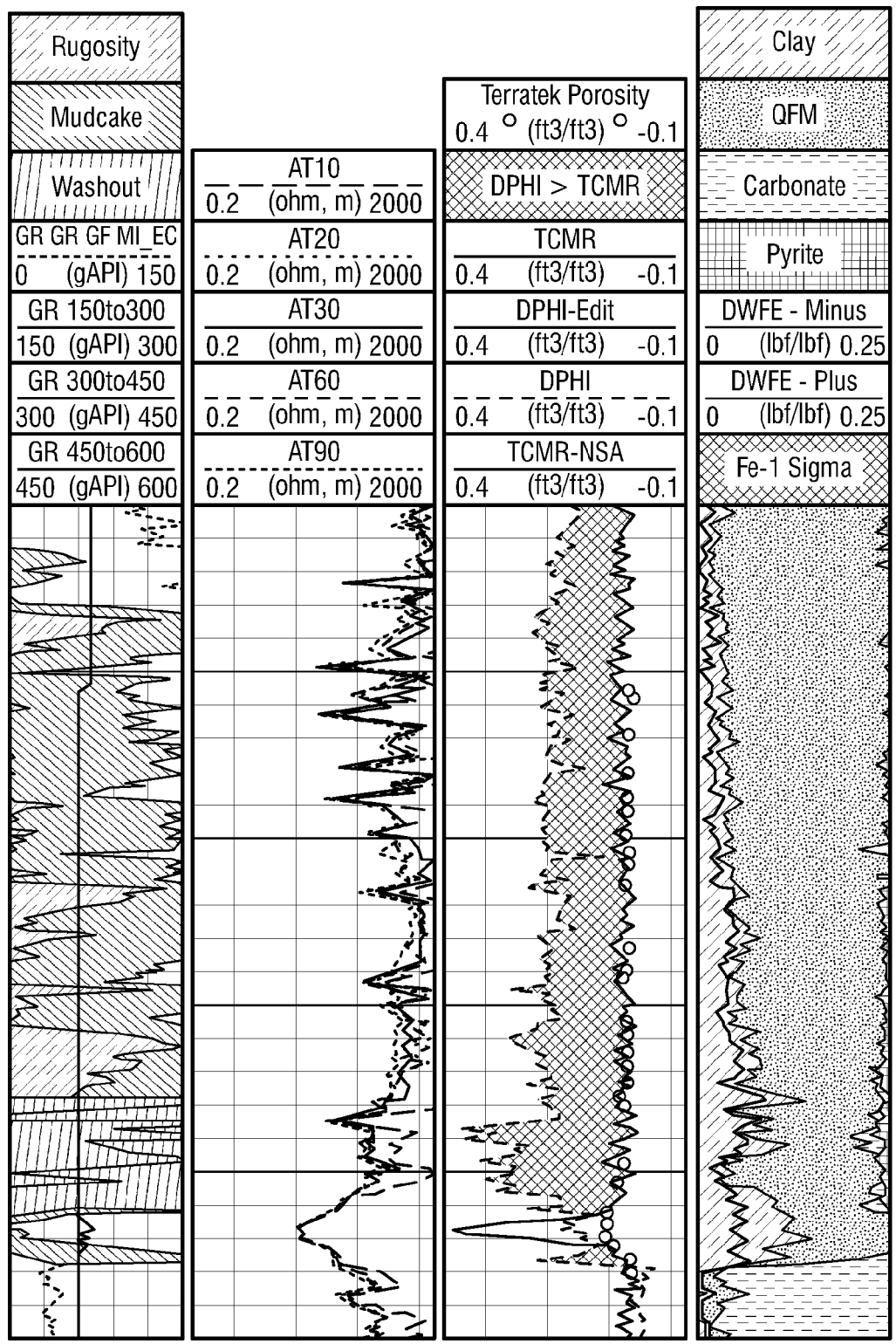
FIGS. 10A and 10B are a total organic carbon (TOC) estimation in organic shale wherein kerogen density RHOk, =1.35 g/cc, maturity constant Kvr=1.2, hydrogen index of the pore fluid HIf=1, and apparent fluid density in total pore volume RHOF=0.8 g/cc.
Figure 10B:
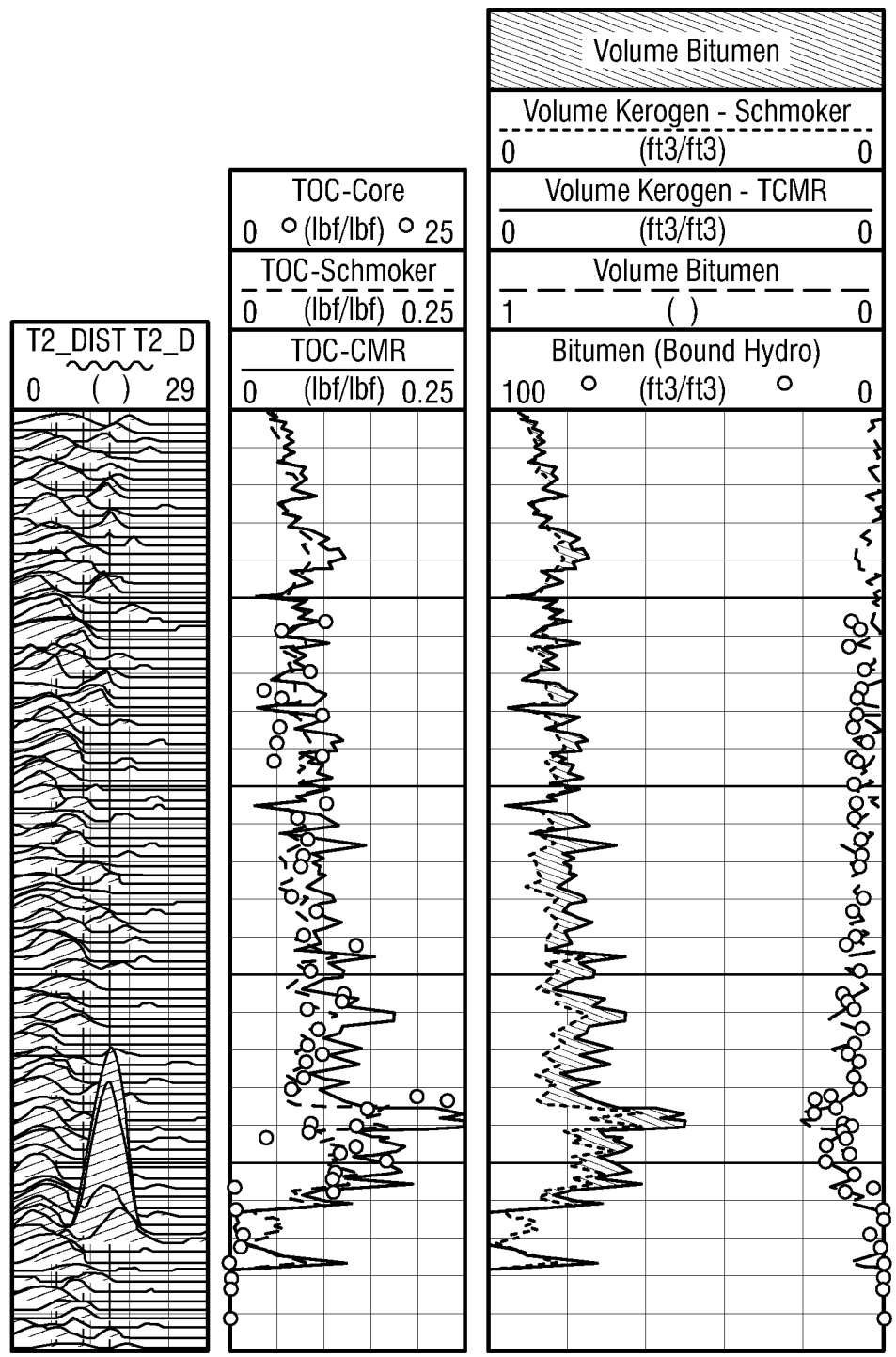

FIG. 8 is a partial log of shale section in a well which shows separation (porosity deficit) between density porosity (DPHI) and TCMR where the kerogen is present. The indicated region where the matrix adjusted density porosity (DPHI) and TCMR are separated reflects potential organic shale. Another log reflects uranium content U which will show an elevated reading in the presence of kerogen. FIG. 9 is a log of a shale section which shows separation between density porosity (DPHI) and TCMR where the kerogen is present. FIGS. 10A and 10B show a log of a TOC estimation in organic shale wherein $\rho_k=1.35$ g/cc, $K_{vr}=1.2$, $HI_f=1$, and $\rho_f=0.8$ g/cc.

According to another aspect, NSA processing may be used to more accurately determine the likelihood of bitumen in a sample. More particularly, significant fractions of bitumen (>5% bulk volume) of the rock are sometimes present in immature organic shale reservoirs. The magnetic resonance determination with NSA processing of total porosity is insensitive to bitumen, and thus, the TOC estimation from the porosity deficit method detailed in equations 10 through equation 12 above includes unseen bitumen. If the TOC estimation from the porosity deficit method is much greater than the TOC estimation from empirical methods, bitumen is likely present. See, Schmoker, J. W. and Hester, T. C, Organic Carbon in Bakken Formation, United States Portion of the Williston Basin, AAPG Bulletin, Vol. 67, No. 12, 2165-2174 (1983).

According to another aspect, the NSA processed porosity determination can be used to provide an indication of thermal maturity of the kerogen in the sample. In particular, intervals dominated by organic hosted porosity are identified when TOC estimations from empirical methods match estimations from the porosity deficit method. Intervals dominated by kerogen hosted porosity have very short $T_2$ times, with the majority of the porosity no more than 10 ms. Conversely, intervals associated with non-kerogen hosted porosity are identified when TOC estimations from density regressions overestimate estimations from the porosity deficit method. Intervals dominated by non-kerogen hosted porosity have longer $T_2$ times, with more porosity above 10 ms. It has been observed that the logarithmic mean of the $T_2$ distribution in intervals dominated by kerogen hosted porosity varies laterally across liquid bearing organic shale reservoirs, and, can be related to maturity. Less mature areas are identified by shorter $T_{2LM}$, while more mature areas are identified by longer $T_{2LM}$.

In another aspect, the NSA processed porosity determination can be used as part of a method of finding montmorillinite in gas or condensate shale reservoirs. More particularly, in gas and condensate bearing reservoirs, the NMR hydrocarbon signal tends to be well separated from the clay bound water signal. The amount of $T_2$ signal below 3 ms can be used as an estimate of the amount of clay bound water in an inorganic shale, gas condensate, or gas reservoir.

As previously set forth, the NSA analysis has the ability to examine very short $T_2$ times. The $T_2$ response associated with the four major clay minerals are as follows:

TABLE 3

| Clay Type | Measured $T_2$ at TE .5 ms | Wet Clay Porosity (pu??) |
|---|---|---|
| Montmorillinite | .3 to 1 ms | ~42 |
| Illite | 1 to 2 ms | ~10 |

TABLE 3-continued

| Clay Type | Measured $T_2$ at TE .5 ms | Wet Clay Porosity (pu??) |
|---|---|---|
| Kaolinite | 8 to 16 ms | ~10 |
| Chlorite | ~5 ms | ~10 |

While the vast majority of the hydrocarbon signal is found above 3 ms, montmorillinite and illite both have clay bound water $T_2$ responses below 2 ms as seen in Table 3. However, an appreciable difference in clay bound water exists between illite and montmorillinite. Thus, at the higher clay levels of organic shale reservoirs, the NSA processing is a good mechanism for identifying montmorillinite. Montmorillinite is detected from an elevated wet clay porosity. The wet clay porosity is determined by taking the NMR porosity beneath 3 ms and dividing by the volume of clay obtained from elemental spectroscopy. If the wet clay porosity is greater than 10 PU, then smectite is present. This method is effective in shaly sands, sands where illite and montmorillinite are the dominant clay and no bitumen is present.

Figure 11A:
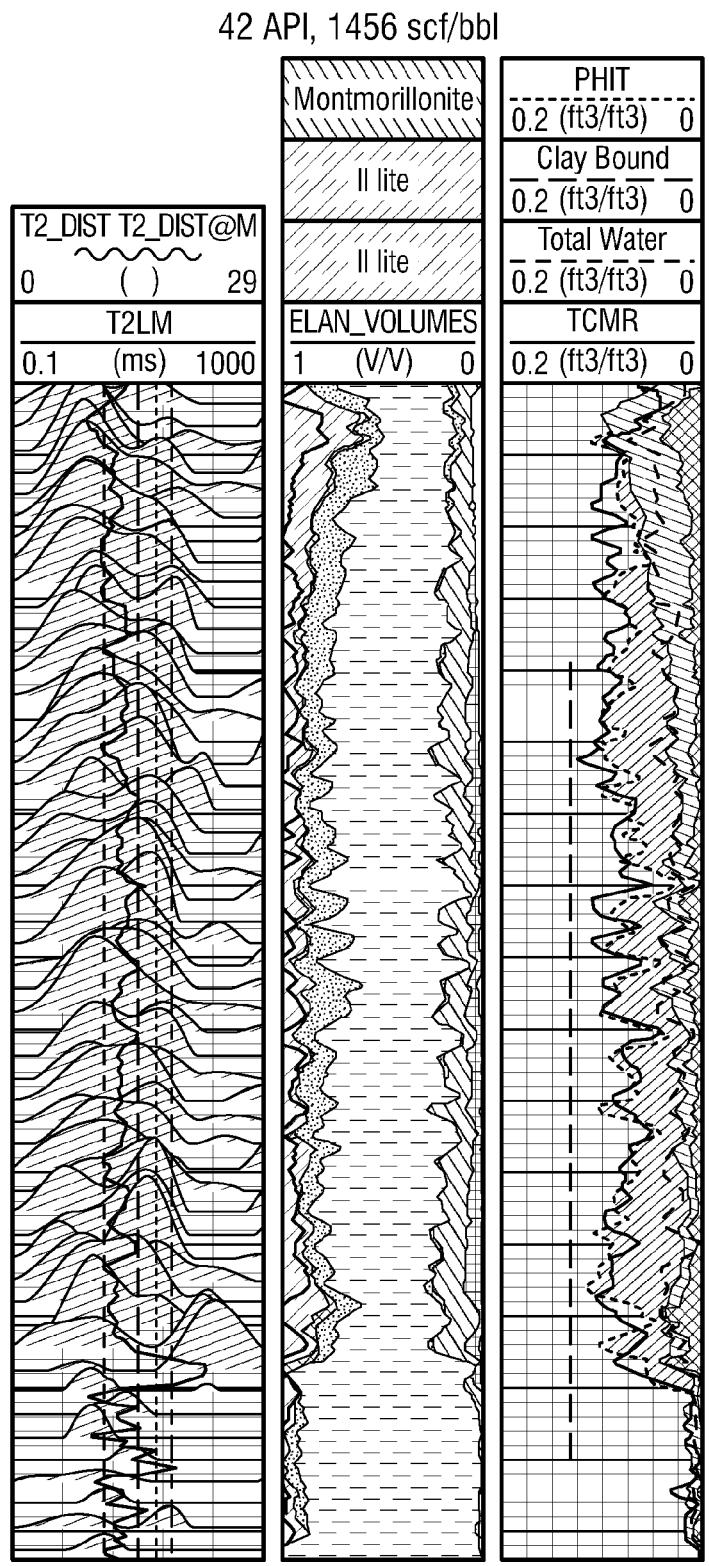
FIGS. 11A, 11B, and 11C are a plot of three ELANs which were run with the same model and then compared to NMR porosity.
Figure 11B:
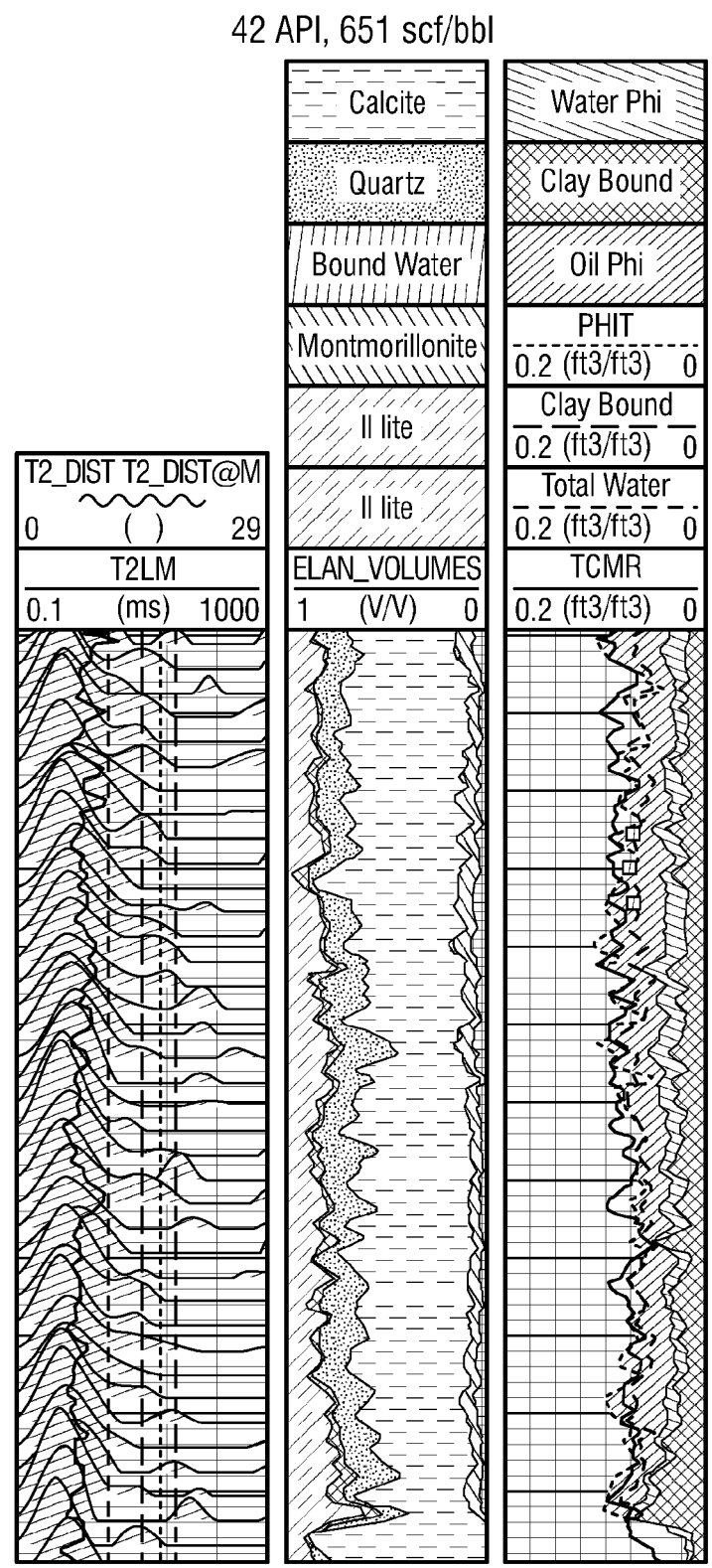
Figure 11C:
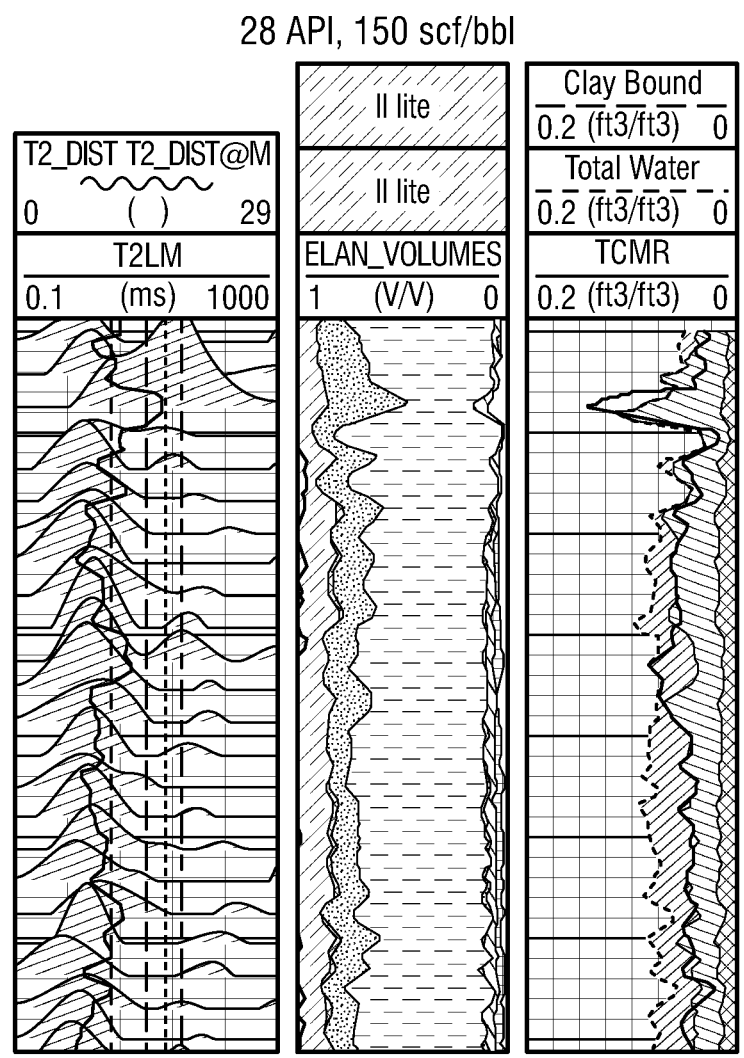
Figure 12:
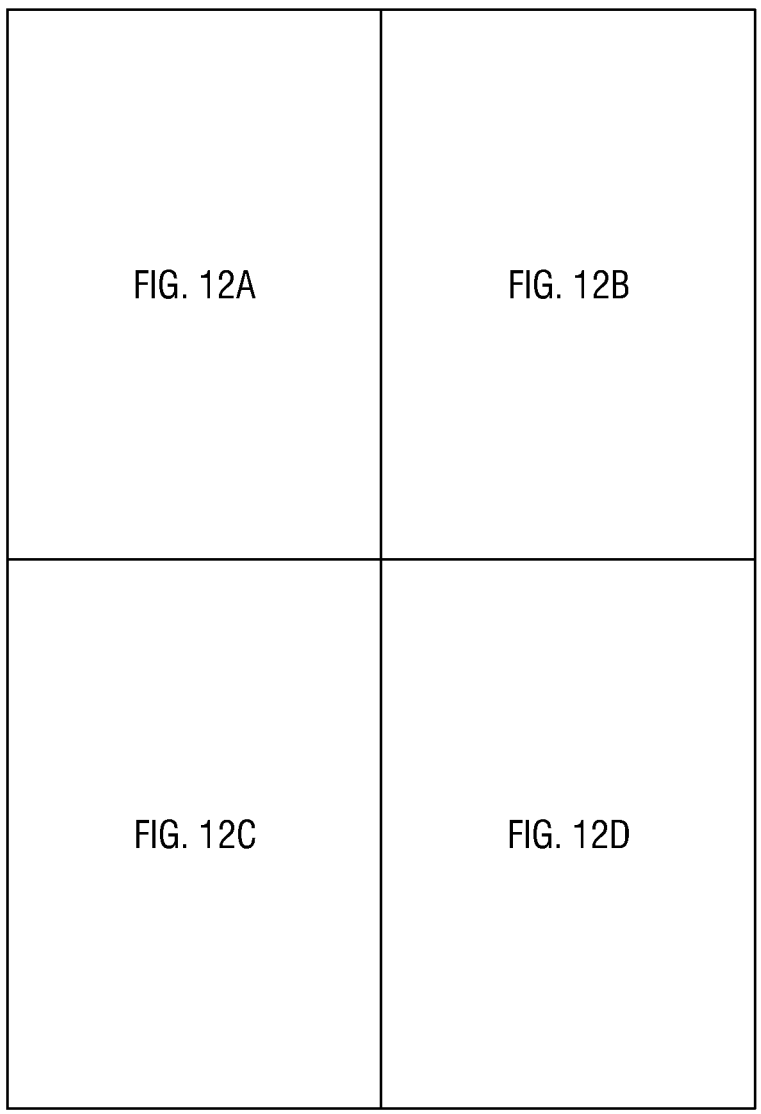
FIGS. 12A, 12B, 12C, and 12D are an ELAN model that shows montmorillinite that was based on and elemental capture spectroscopy (ECS) and triple combo log.
Figure 12A:
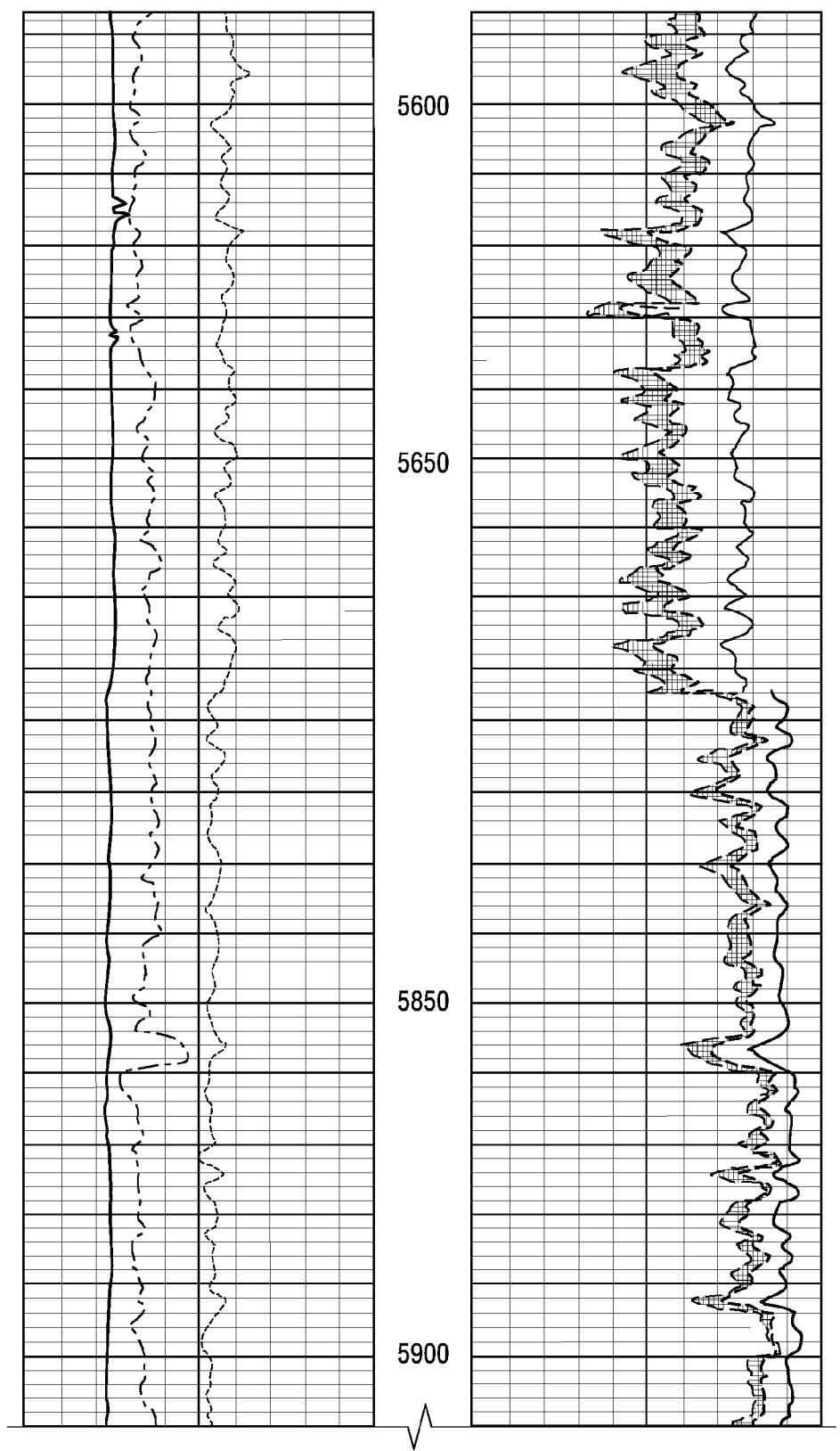
Figure 12B:
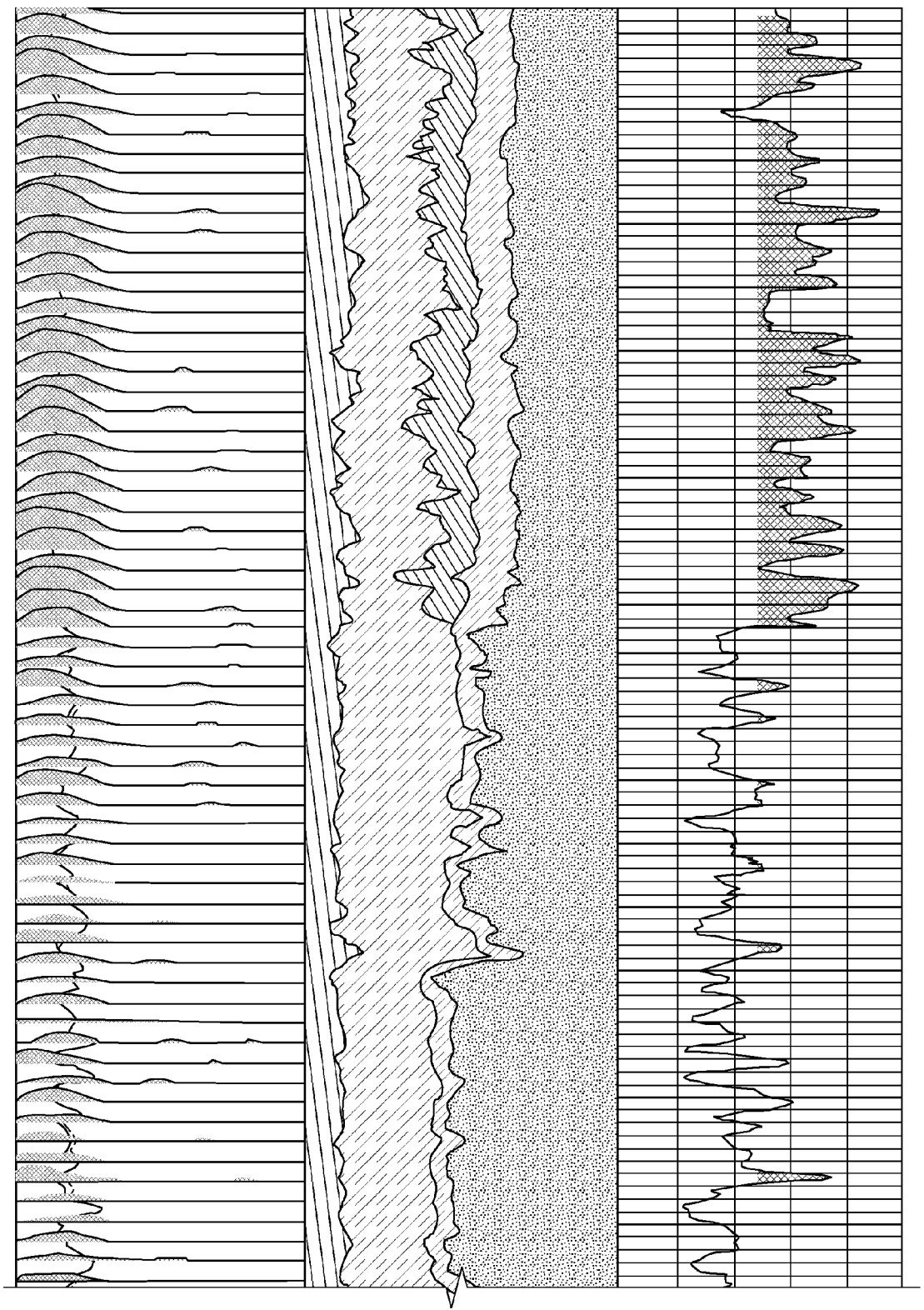
Figure 12C:
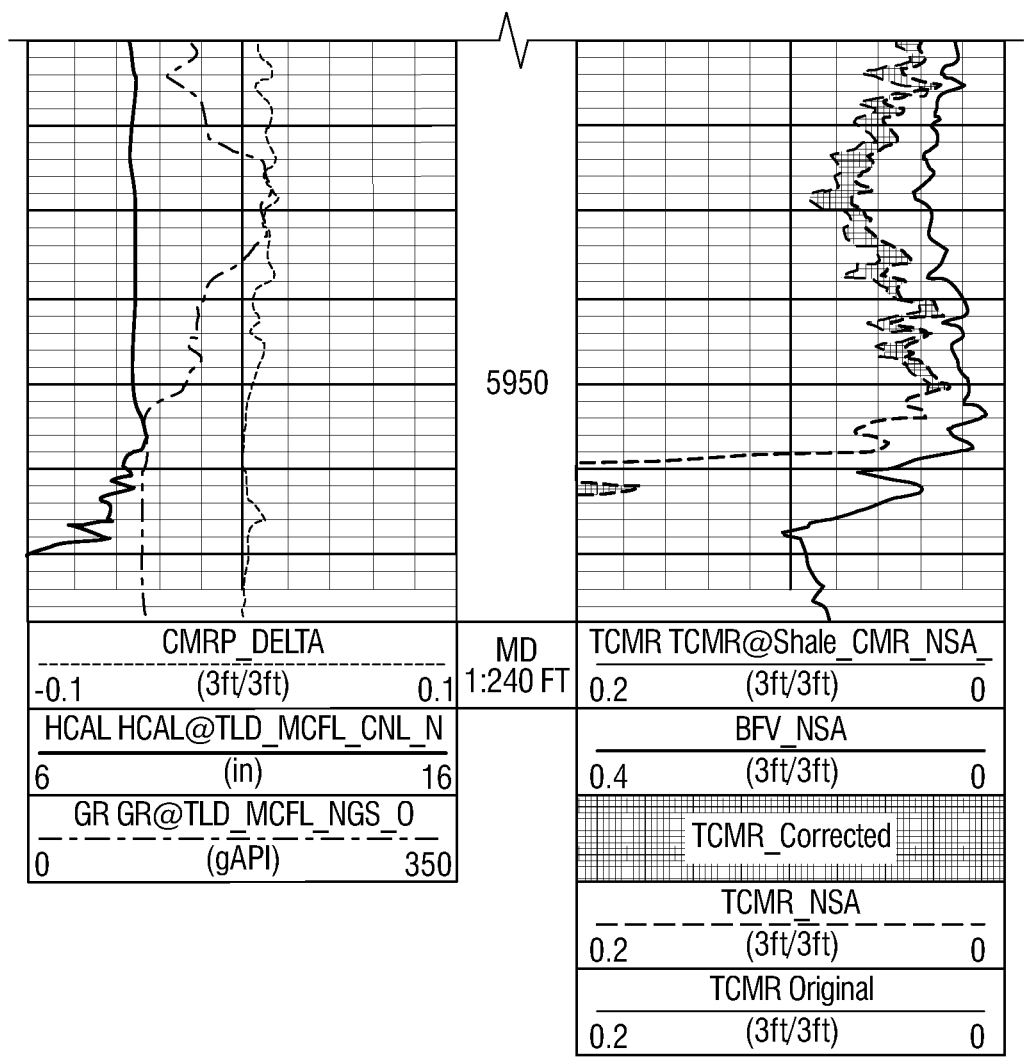
Figure 12D:
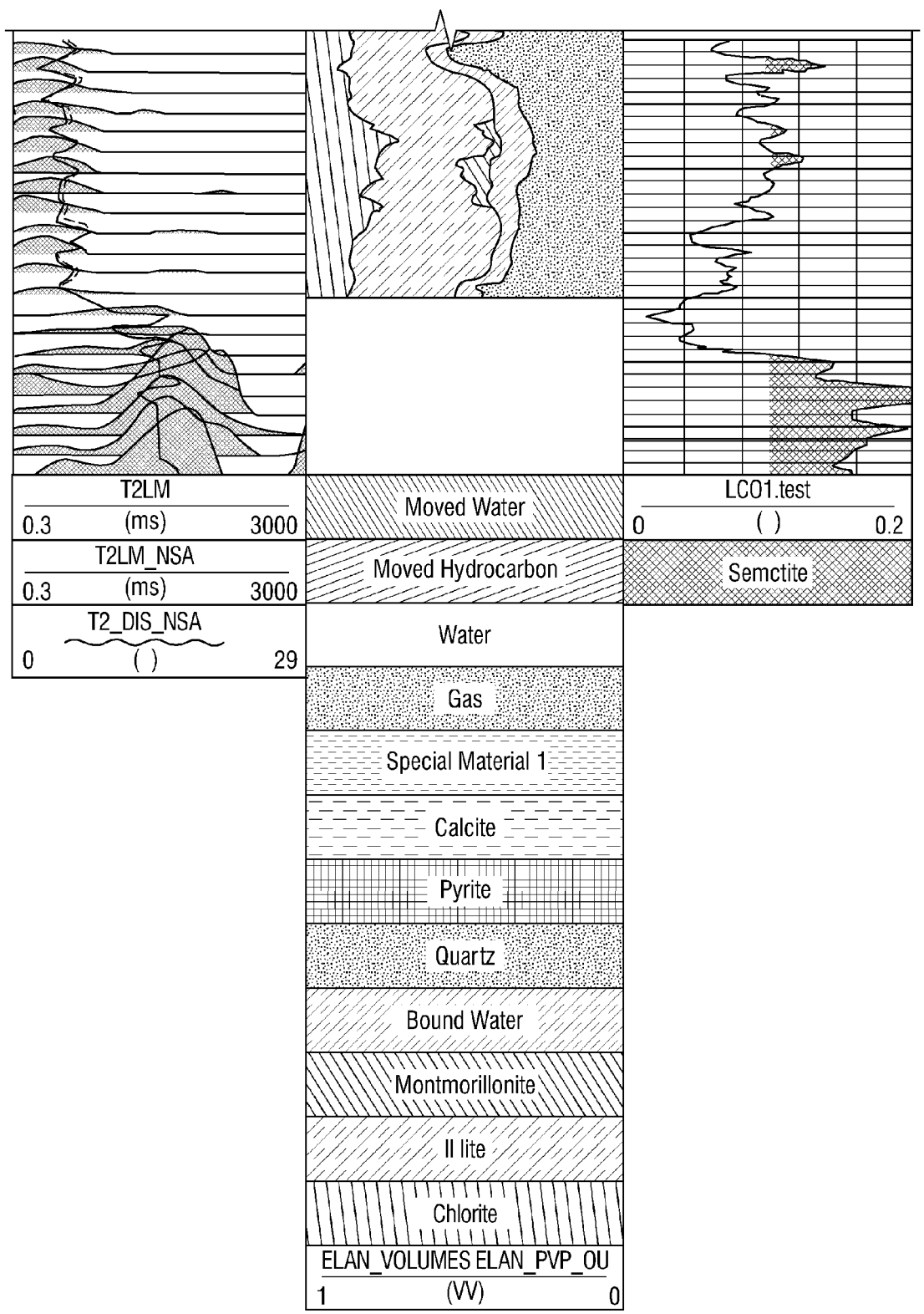

FIGS. 11A, 11B, and 11C represent three ELANs (i.e., probabilistic analyses using statistical methods designed for quantitative formation evaluation, where simultaneous equations described by one or more interpretation models are solved with log measurements and response parameters being used together in response equations to compute volumetric results for formation components). The ELANs were run with the same model and then compared to the NMR derived porosity. The Schmoker relationship (see Schmoker, J. W. and Hester, T. C, Organic carbon in Bakken Formation, United States portion of the Williston Basin, AAPG Bulletin, Vol. 67, No. 12, 2165-2174 (1983)) was used as an input for kerogen volume. In the left and middle ELAN logs (highest and middle maturity examples), there is a reasonable match between NMR porosity and ELAN porosity in the last column (solid and dotted black trace) indicating that the NMR is seeing the majority of the hydrocarbon. In addition, there is a large shift in the $T_2$ distribution to shorter $T_{2LM}$ times from the left figure to the middle figure due to both smaller kerogen pore size and lower gas oil ratio (GOR) which are a result of lower thermal maturity. In the rightmost ELAN log (the lowest maturity example), CMR porosity underestimates total porosity (in the last column the dotted black trace is large than the solid black trace). It may therefore be inferred that the $T_2$ times of the kerogen hosted pores are so short, they are not detected by the CMR tool. Thus, the $T_2$ distribution in the right-most ELAN log represents primarily the clay and capillary bound water in the formation.

FIGS. 12A, 12B, 12C, and 12D are an ELAN model log that shows montmorillinite that was based on an Elemental Capture Spectroscopy (ECS—a trademark of Schlumberger) log and triple combo log. The wet clay porosity (curve on the right) was estimated by taking the NSA porosity below 3 ms and dividing by the weight of clay from the ECS. When the estimated wet clay porosity from the NSA analysis and ECS exceeds 10 pu, montmorillinite is present. It is noted that the NSA porosity is substantially greater than NMR standard porosity in zones with montmorillinite.

According to another aspect, a quality flag or indicator may be provided to identify intervals of a formation where the NSA analysis may be significantly underestimating the formation porosity. More particularly, the NSA analysis provides a good estimate of formation porosity in shales. However, the porosity still may be underestimated due to extremely short $T_2$ times that even the NSA analysis cannot account for because the relaxation times are significantly shorter than the echo spacings. By taking the difference in the NSA analysis versus the ILT algorithm, intervals of a formation may be identified where the NSA may have large underestimations of formation porosity. Those intervals are where the difference between porosity as determined by the NSA analysis and the ILT analysis is largest. A quality flag or indicator can be used to identify those locations.

There have been described and illustrated herein several embodiments of methods of investigating a formation using NMR measurements. While particular embodiments and aspects have been described, it is not intended that the disclosure be limited thereto, and it is intended that the claims be as broad in scope as the art will allow and that the specification be read likewise. Thus, while particular correction factors for modifying porosity estimates at short $T_2$ have been described, it will be appreciated that other correction factors may be utilized. Likewise, while particular pulse sequences have been described for obtaining NMR signals from which a porosity determination can be made, it will be appreciated that other such sequences can be utilized. Further, while the corrected porosity determination (NSA) was described as being useful to obtain improved determinations of particular sample parameters such as rock permeability, hydrocarbon viscosity, and bound and free fluid volumes, and improved analysis of organic content of a sample or formation, it may also be useful in obtained improved determinations of other sample or formation parameters and content. Further yet, it should be appreciated that the described methods can be adapted and applied to any measurements of longitudinal relaxation time $T_1$ and diffusion D as well. When the $T_1$ relaxation is short and is on the order of the polarization time, or when diffusion is large and can significantly reduce the exponent in the diffusion kernel, a correction factor for porosity sensitivity can be computed from the normalized bias obtained from the porosity sensitivity curve. This correction factor can subsequently be used to compute a more accurate value of porosity. Likewise, it will be appreciated that the described methods can be extended to compute correction factors for two and three dimensional measurements such as D-T1, D-T2, T1-T2, D-T1-T2, where D refers to diffusion and T1 and T2 refer to longitudinal and transverse relexation. It will therefore be appreciated by those skilled in the art that yet other modifications could be made. Accordingly, all such modifications are intended to be included within the scope of this disclosure as defined in the following claims. In the claims, means-plus-function clauses, if any, are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of investigating a geological formation traversed by a borehole, comprising:
    a) obtaining a nuclear magnetic resonance (NMR) tool;
    b) subjecting a sample of known porosity to a nuclear magnetic resonance (NMR) sequence with a pulse echo spacing using the NMR tool;
    c) determining a normalized bias $B(T_2)$ of said NMR tool as a function of $T_2$ relaxation times;
    d) locating the NMR tool in the borehole and detecting signals in response to said NMR sequence at at least one depth in the borehole;

e) analyzing a decay of the detected signals with a computer processor, in order to extract a distribution of the $T_2$ relaxation times; and f) computing and providing, with the computer processor, a value for porosity of the formation at said depth as a function of at least one of said $T_2$ relaxation times, wherein said computing utilizes a correction factor that modifies the value of the parameter as a function of the $T_2$ relaxation time for at least the $T_2$ relaxation times occurring on the order of said pulse echo spacing, wherein said correction factor is a function of said normalized bias.

2. A method according to claim 1, wherein:
said pulse echo spacing is approximately 0.2 ms, and
said relaxation times on the order of said pulse echo spacing are 1 ms and less.

3. A method according to claim 1, wherein:
said correction factor is $c_f(T_2)=1/(1+B(T_2))$.

4. A method according to claim 2, wherein:

$$B(T_2) \approx \frac{\hat{\phi}(T_2) - \phi_T}{\phi_T}$$

where $\phi_T$ and $\hat{\phi}(T_2)$ are respectively a true and an estimated porosity of a calibration sample obtained from a porosity sensitivity curve for said NMR tool.

5. A method according to claim 1, wherein:
said correction factor is $$c_f(T_2) = \frac{1}{1 + B(T_2)\frac{R(T_2)}{\beta(R(T_2)) + R(T_2)}}$$

where $R(T_2) = \frac{\hat{\phi}(T_2)}{\sigma_\phi(T_2)}$ and corresponds to a signal to noise ratio for a given $T_2$, $\beta$ is a scalar, $<\ >$ is an average computed over $T_2$, $$B(T_2) \approx \frac{\hat{\phi}(T_2) - \phi_T}{\phi_T}$$

is the relative bias obtained from an NMR sensitivity curve of said NMR tool where $\phi_T$ is a true porosity of a calibration sample and $\hat{\phi}(T_2)$ is an estimated porosity of the calibration sample, and $\sigma_\phi$ is a standard deviation of the estimated porosity.

6. A method according to claim 5, wherein:
said correction factor tends to a value of 1 with respect to a particular $T_2$ relaxation time when said signal to noise ratio is small for that particular $T_2$ relaxation time.

7. A method according to claim 1, further comprising:
using said value of porosity obtained utilizing said correction factor in order to obtain determinations of at least one additional parameter of said sample at said depth.

8. A method according to claim 7, wherein: said at least one additional parameter of said sample is one of rock permeability, hydrocarbon viscosity, bound fluid volume, and free fluid volumes.

9. A method according to claim 7, wherein: said at least one additional parameter of said sample is organic content of said sample.

10. A method according to claim 7, wherein: said at least one additional parameter of said sample is montmorillinite content.

* * * * *